United States Patent [19]

Perkins

[11] Patent Number: 5,401,272
[45] Date of Patent: Mar. 28, 1995

[54] MULTIMODALITY PROBE WITH EXTENDABLE BIPOLAR ELECTRODES

[75] Inventor: Rodney C. Perkins, Woodside, Calif.

[73] Assignee: Envision Surgical Systems, Inc., Palo Alto, Calif.

[21] Appl. No.: 197,357

[22] Filed: Feb. 16, 1994

Related U.S. Application Data

[63] Continuation of Ser. No. 951,457, Sep. 25, 1992, abandoned.

[51] Int. Cl.$^6$ .................. A61B 17/32; A61B 17/39
[52] U.S. Cl. .................. 606/15; 606/50; 606/51
[58] Field of Search .................. 606/14–16, 606/42, 45–52; 604/35

[56] References Cited

U.S. PATENT DOCUMENTS

| | | | |
|---|---|---|---|
| 3,858,586 | 1/1975 | Lessen | 606/49 |
| 4,016,881 | 4/1977 | Rioux et al. | 606/51 |
| 4,418,692 | 12/1983 | Guay | 606/51 X |
| 4,660,571 | 4/1987 | Hess et al. | 606/16 X |
| 4,674,499 | 6/1987 | Pao | |
| 4,823,791 | 4/1989 | D'Amelio et al. | |
| 4,936,842 | 6/1990 | D'Amelio et al. | |
| 5,186,714 | 2/1993 | Boudreault et al. | 606/15 X |
| 5,267,994 | 12/1993 | Gentelre et al. | 606/41 |

FOREIGN PATENT DOCUMENTS 2194748 3/1988 United Kingdom .................. 606/49

OTHER PUBLICATIONS

Kimura et al, "Use of Gas Jet . . . ", IEEE Trans. on Bio Med Eng, vol. BME-25, No. 3, May 1978, pp. 281-224.

Primary Examiner—Lee S. Cohen
Attorney, Agent, or Firm—Haynes & Davis

[57] ABSTRACT

A surgical probe, and procedure using the same, enabling a surgeon to cut body tissue by delivering energy, such as a laser beam, to the body tissue and without removing the instrument to cauterize the body tissue by direct application of electric current. The surgical probe includes an elongated member having a fiber optic positioned on a longitudinal axis of the elongated member and pair of elongated electrodes that span an entire length of the elongated member. The elongated electrodes slide lengthwise in a direction parallel to the longitudinal axis. During cutting procedures, the distal ends of the electrodes are in a retracted position not beyond the distal end of the elongated member, and during cauterization procedures, the distal ends of the electrodes are in an extended position beyond the distal end of the elongated member. In a preferred embodiment, the distal ends of the electrodes are pre-bent so as to converge toward each other as they are extended beyond the distal end of the elongated member.

5 Claims, 6 Drawing Sheets

MULTIMODALITY PROBE WITH EXTENDABLE BIPOLAR ELECTRODES

This application is a continuation of application Ser. No. 07/951,457, filed Sep. 25, 1992, now abandoned.

FIELD OF THE INVENTION

The present invention relates generally to electrosurgical devices, and more particularly to multimodal energy delivering probes used for precision cutting, electrocauterization, electrocoagulation, irrigation, ablation, and aspiration procedures.

BACKGROUND OF THE INVENTION

Fiber optic delivery systems have gained wide spread popularity in recent years for conventional laser surgery procedures. These devices are typically probes with optical fibers for transmitting laser energy to a specific location within a body of a patient in order, for example, to cut or coagulate body tissue.

A distal end or tip of an optical fiber probe may have different designs depending upon the specific mode of treating a problem area. "Noncontact" laser probes are designed to treat problem areas by delivering laser energy to cut or coagulate body tissue spaced away from the probe tip. "Contact" or "hot tip" laser probes are designed to treat problem areas in physical contact with body tissue by delivery of laser energy to heat a probe tip, as well as directly into treated tissue.

While both noncontact and contact laser probes are very effective at precisely cutting and coagulating body tissue, it is sometimes necessary to cauterize specific areas of treated tissue by applying an electric current. However, cauterizing tissue by direct application of electric current typically requires a surgeon to first remove the laser probe, and then insert a different probe for cauterization. The removal and insertion of different probes increases the time of a medical procedure, increases discomfort to a patient, and increases complexity of the overall procedure.

The design of such probes is further complicated by such needs as the ability to irrigate to clear fluid for visualization and progressive dissection. Other tools may also be required in a given procedure.

SUMMARY OF THE INVENTION

In view of the foregoing, the present invention provides a unitary, surgical tool that enables a surgeon to precisely cut, ablate, coagulate, and cauterize body tissue by direct application of both laser energy and electric current without having to remove the surgical tool or probe from a patient between each of these procedures. In addition to these procedures, the present invention also enables a surgeon to irrigate and aspirate a treated area using the same surgical tool. The invention may be used in multiple endoscopic applications including, but not limited to, laproscopic cholecystectomy.

Briefly, the present invention provides a probe having an elongated member, with an energy delivery device, such as a fiber optic, positioned along a longitudinal axis of the member, and a pair of elongated electrodes that span the length of the elongated member. The elongated electrodes slide lengthwise in a direction parallel to the longitudinal axis of the elongated member. In an extended position, distal ends of the electrodes extend beyond a distal end of the elongated member, and in a retracted positioned the distal ends of the electrodes are positioned behind, or at least adjacent to, the distal end of the elongated member.

In accordance with the invention, the electrodes have a retracted position avoiding interference with the energy delivery device during surgical procedures, such as cutting body tissue. When electro-cauterization is required, the electrodes are extended beyond the distal end of the elongated member in order to be appropriately positioned for contacting and cauterizing the body tissue.

According to one aspect of the invention, the distal ends of the electrodes are pre-bent so that they approach each other as the distal ends of the electrodes are slid past the distal end of the elongated member. In one alternative mode, the electrodes converge and make contact, and are then used as a unipolar electrode.

An irrigation channel and an aspiration channel are also provided in one embodiment of the elongated member for irrigating and aspirating body tissue that is to be treated. Also, an additional lumen for an argon ion coagulator and/or a gas jet lumen may be provided.

According to a further aspect of the invention, the distal end of the elongated member forms a blade in order to enable a surgeon to ablate tissue.

Accordingly, a fully functional, unitary, surgical tool is provided capable of both laser surgery, for example, using an argon laser, and electrocauterization, and argon beam coagulation.

Other aspects and advantages of the present invention can be seen upon review of the figures, the detailed description, and the claims to follow.

DESCRIPTION OF THE PREFERRED EMBODIMENTS

Figure 1:
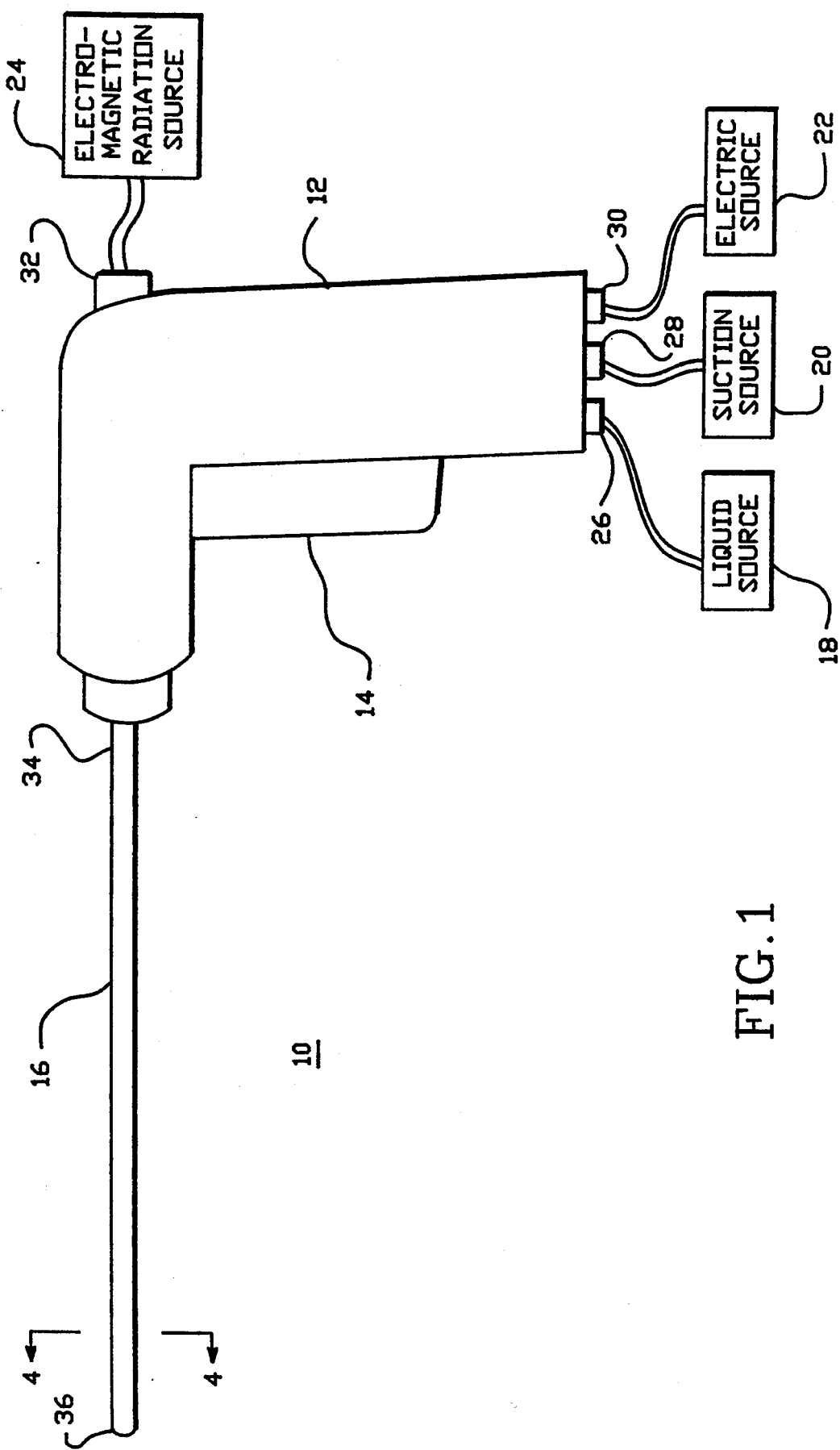
FIG. 1 is an elevational view of a laser probe configured in accordance with the present invention.

A detailed description of preferred embodiments of the present invention is provided with respect to FIGS. 1-8. FIGS. 1-8 illustrate preferred embodiments of a laser probe having extendable bipolar electrodes constructed in accordance with the present invention. Referring first to FIG. 1, a hand-held portion of a laser probe 10 configured in accordance with the present invention is illustrated. The laser probe 10 includes a handle 12 (heuristic illustration) having an actuator, or trigger 14, and an elongated member 16. The elongated member 16 has a proximal end 34 and a distal end 36. The elongated member 16 is to be inserted into a patient through a small orifice or incision in the body of the patient. The probe can be used as handheld multi-functional surgical dissection device, as well as an endoscopic device.

The handle 12 also includes several input ports which are to be connected to outputs of various sources. These sources include, for example, a liquid source 18 (for irrigation), a suction source 20 (for aspiration), an electric source 22 (for cauterization), and an electromagnetic radiation source 24 (laser source). Other ports may be included, such as a gas jet source and an argon laser port, as discussed below. As illustrated, these sources 18, 20, 22, and 24 are to be connected to the handle inputs 26, 28, 30, and 32 respectively.

The handle 12 is constructed of conventional materials known in the art, such as plastic, ceramic, or metal. Similarly, the elongated member 16 is constructed of materials typically used in similar devices.

Figure 1A:
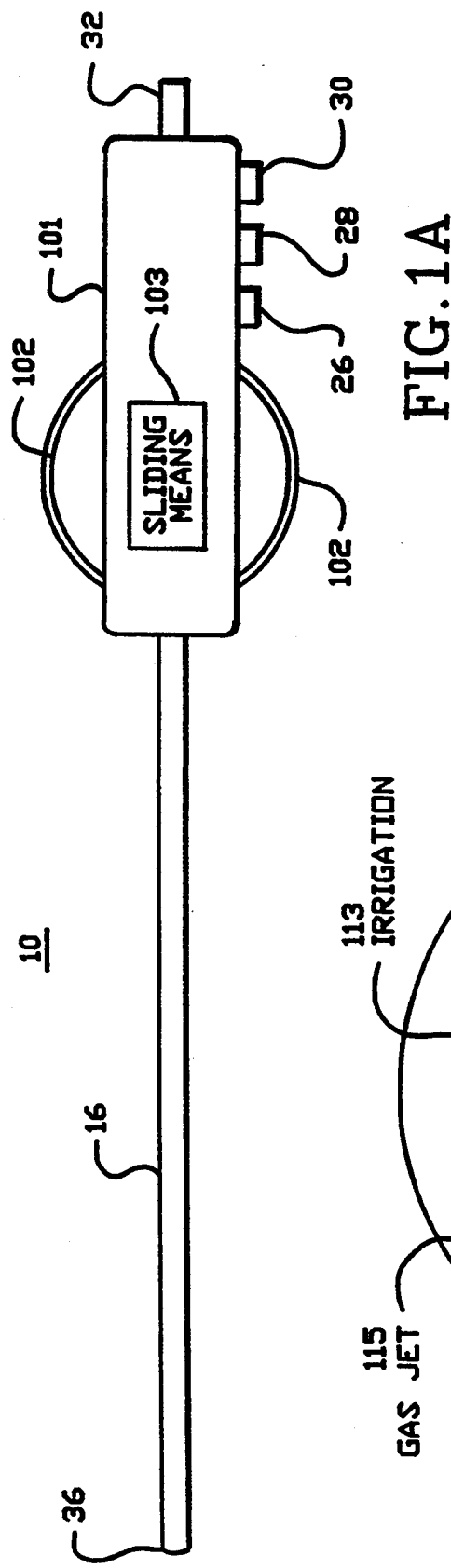
FIG. 1A is an elevational view of another embodiment of the present invention.

FIG. 1A illustrates a preferred embodiment of a handle 101 of the probe 10. Similarly to the handle 12 illustrated in FIG. 1, the handle 101 includes input ports 26, 28, 30, and 32. The handle 101 includes opposing bowed members 102, which are operated by squeezing like forceps to extend the electrodes. When the bowed members 102 are squeezed together, the action advances the bipolar electrode tips outward from the distal end of the probe.

FIG. 1A illustrates a block diagram 103 of means for sliding the elongated electrodes in response to movement of the members 102. The internal mechanics for sliding the elongated electrodes in response to squeezing the members 102 can be readily constructed by persons skilled in the art.

Figure 2A:
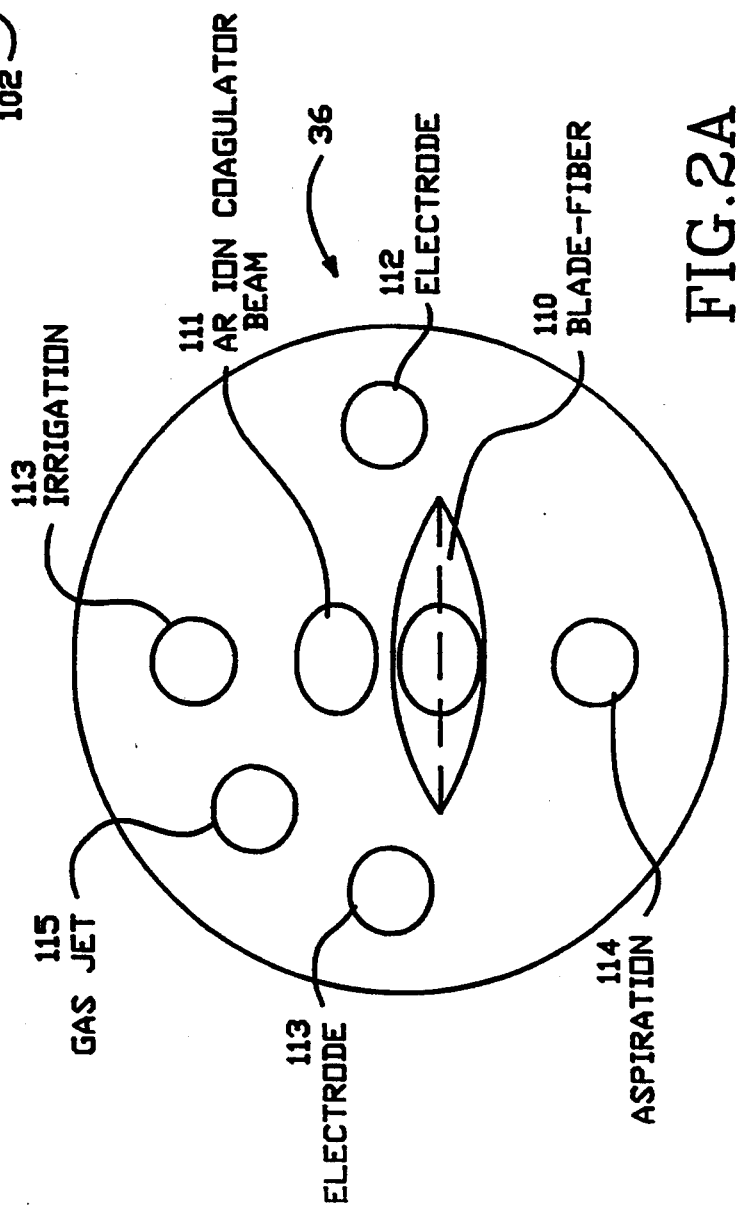
FIG. 2A is an end view of another embodiment of the probe.
Figure 2:
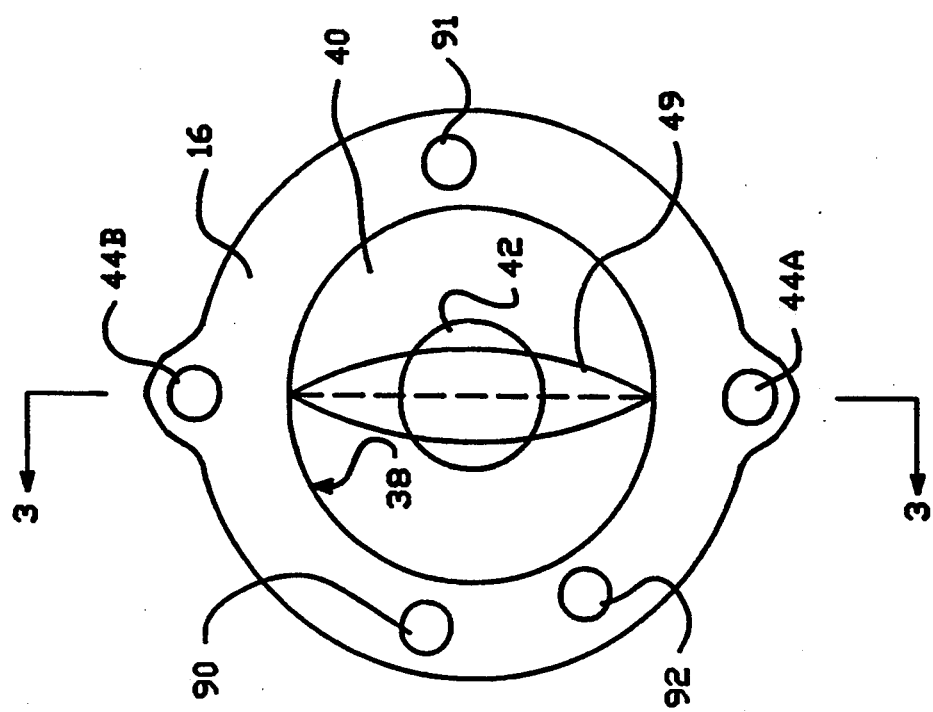
FIG. 2 is an end view of one embodiment of the laser probe shown in FIG. 1.

FIG. 2 illustrates an end view of one embodiment of the distal end 36 of the elongated member 16. Inner walls 38 of the elongated member 16 are shown to define an inner lumen 40 that extends the entire length of the elongated member 16 between the distal end 36 and the proximal end 34. As shown in FIG. 2, an energy delivery device, or optic fiber 42 is within lumen 40. The optic fiber 42 can be rigidly secured within the lumen 40. In a preferred embodiment, the fiber optic 42 is to be positioned along a longitudinal axis 41 (FIGS. 3 and 5) of the elongated member 16. A proximal end of the fiber optic 42 is connected to the electromagnetic radiation source (laser source) according to known techniques. The optic fiber would be rigidly fixed and suitable means for transmission of energy to the optic blade 49 is included. Alternatively, a removable, sharpened fiber may be used instead of the blade-fiber mechanism.

The liquid source 18 is connected to lumen 90 and the suction source 20 is connected to the lumen 91 according to known techniques to provide means for irrigating and/or aspirating a region near the distal end 36 of the elongated member 16. Lumen 92 provides an optical path for an argon ion laser coagulator.

According to the present invention, a pair of electrode lumens 44 are provided which extend the length of the member 16 in a direction parallel with the member 16 and the lumen 40.

FIG. 2A is an end view of the distal end 36 of probe 16 in yet another alternative embodiment. In the embodiment of FIG. 2A, the probe includes a blade-fiber mechanism 110, such as that described with respect to FIG. 2. The blade-fiber mechanism 110 is offset slightly from the center of the probe. Mounted next to the blade-fiber mechanism 110 is a lumen 111 for an argon ion coagulator beam. Lumens 112 and 113 are provided for the bipolar electrodes. Lumen 113 is provided for use in irrigation, and lumen 114 is provided for use in aspiration. Further, a gas jet lumen 115 is provided so that a jet of gas may be used to clear debris or other material from the blade of the blade-fiber mechanism 110 or from the tissue itself.

Figure 3:
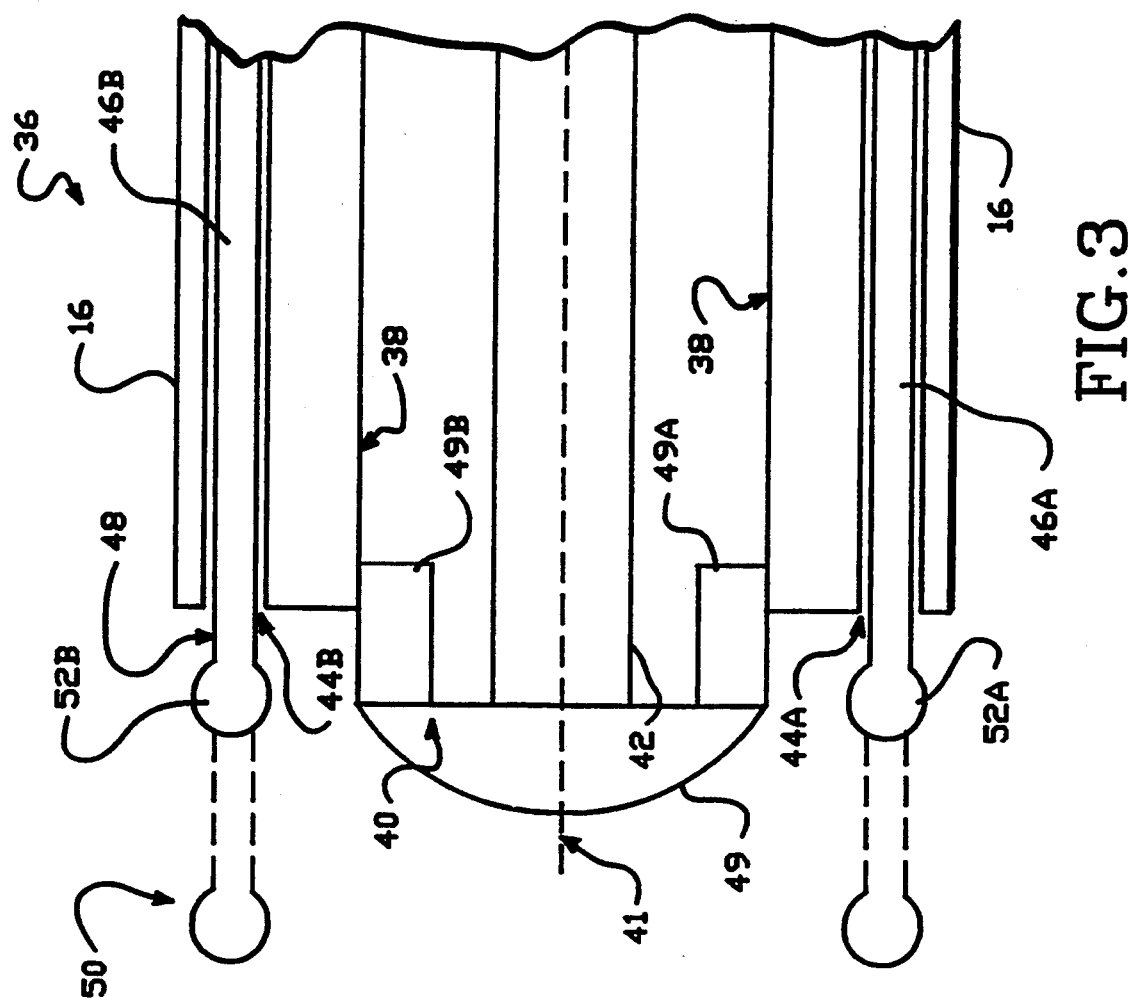
FIG. 3 is a longitudinal section view of a tip of the laser probe of FIG. 2 taken along line 3—3.

FIG. 3 illustrates a longitudinal section view of the distal end 36 of probe 16 of FIG. 1, configured as shown in FIG. 2. Fiber 42 is coupled to blade 49, which is secured within lumen 40 by members 49A, 49B, which may be threaded or otherwise secured to the probe 16, on wall 38 of lumen 40. Electrodes 46A and 46B are mounted within lumens 44A and 44B.

In accordance with the present invention, means are provided for cutting, coagulating, and cauterizing tissue by direct application of both laser energy and electric current using the same surgical tool. Referring to FIG. 3, cauterization by direct application of electric current is provided by the elongated electrodes 46 which are slidably secured within the electrode lumens 44A, 44B, thus enabling the elongated electrodes 46A, 46B to retract to a position 48 and extend longitudinally to a position 50 (shown in phantom) during various surgical procedures. Distal ends 52A, 52B of the elongated electrodes 46A, 46B are exposed, and a remainder of the electrodes 46 are insulated from the environment, preferably by being located within the electrode lumens 44A, 44B.

The electrodes 46A, 46B are constructed of materials known in the art for such applications. Similarly, portions of the elongated electrodes can be insulated by an outer, nonelectrically conducting casing.

Figure 4:
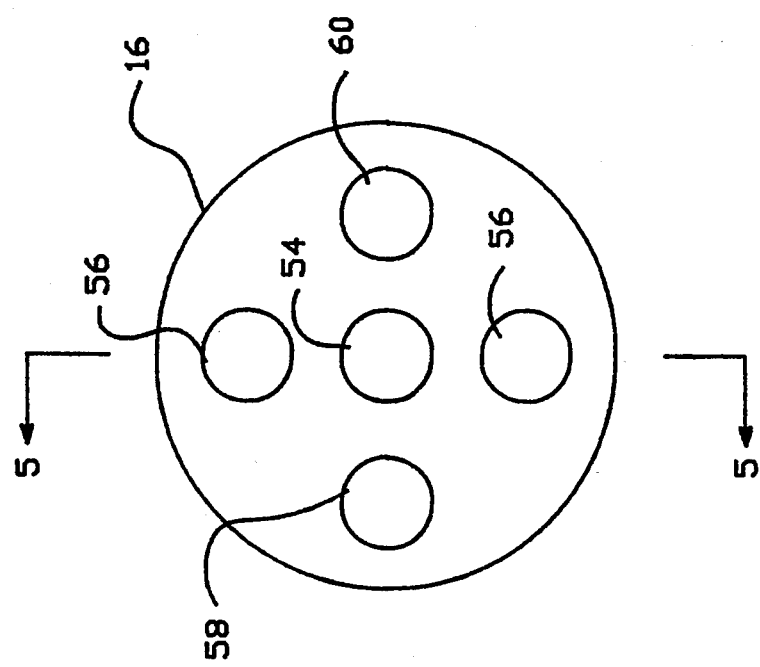
FIG. 4 is a cross-sectional view of another embodiment of the laser probe of FIG. 1 taken along line 4—4.

FIG. 4 illustrates a cross-sectional view of another embodiment near the distal end 36 of the elongated member 16 showing the lumens in one embodiment. This embodiment includes five (5) lumens which run parallel to the longitudinal axis 41 (see FIG. 3) of the member 16 and extend the entire length between the distal end 36 and the proximal end 34. A fiber optic lumen 54 is located in the center of the member 16 along the longitudinal axis 41 in this embodiment. At opposing sides and running parallel to the lumen 54 are electrode lumens 56. A fiber optic (not shown) lies within lumens 54 and a pair of electrodes (not shown) are located within the lumens 54 and 56, respectively. FIG. 4 also illustrates lumens 58 and 60 which provide means for communicating with the liquid source 18 for irrigation and the suction source for aspiration 20, respectively. In yet another alternative, the irrigation and aspiration lumens may be concentric with the fiber optic lumens. A gas jet may be used in place of the suction source 20 in an alternative system.

Figure 5:
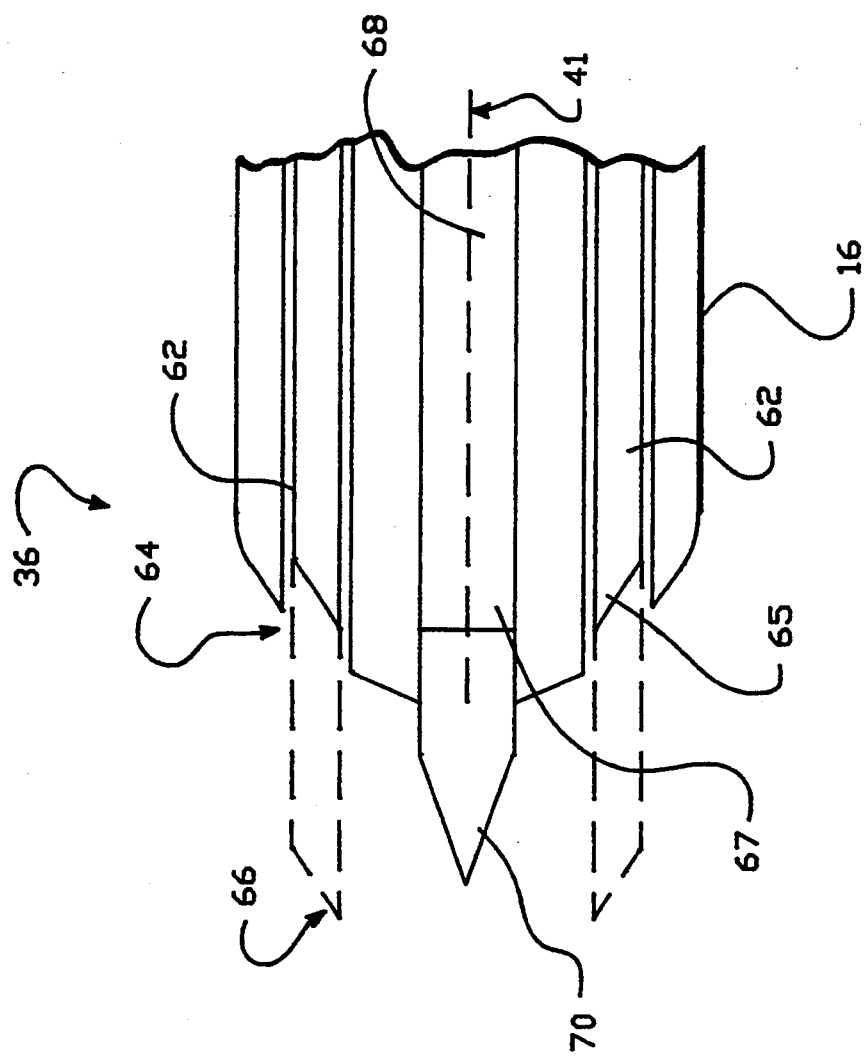
FIG. 5 is a longitudinal section view of a tip of the laser probe taken along line 5—5 of FIG. 4.

FIG. 5 is a longitudinal sectional view taken along line 5—5 of FIG. 4 and extending to the distal end 36 of member 16. A fiber optic 68 and elongated electrodes 62 are shown in FIG. 5, in their retracted position 64 in solid lines, and in the extended position 66, in phantom. The distal ends 65 of the elongated electrodes 62 are illustrated as being pointed, however, the distal ends 65 can be flat or round in other embodiments.

The fiber optic 68 within the lumen 54 has a distal end 67 connected to a tip 70. The tip 70 can be secured to the distal end of the elongated member by known techniques, such as being threaded so that the tip 70 may be screwed into the distal end 36 of the elongated member 16. The tip 70 may behave as a lens, as a hot tip, or as a mechanical blade depending upon the particular application. The tip 70 may be manufactured of quartz, sapphire, graphite, diamond, glass or other hard materials.

Figure 6:
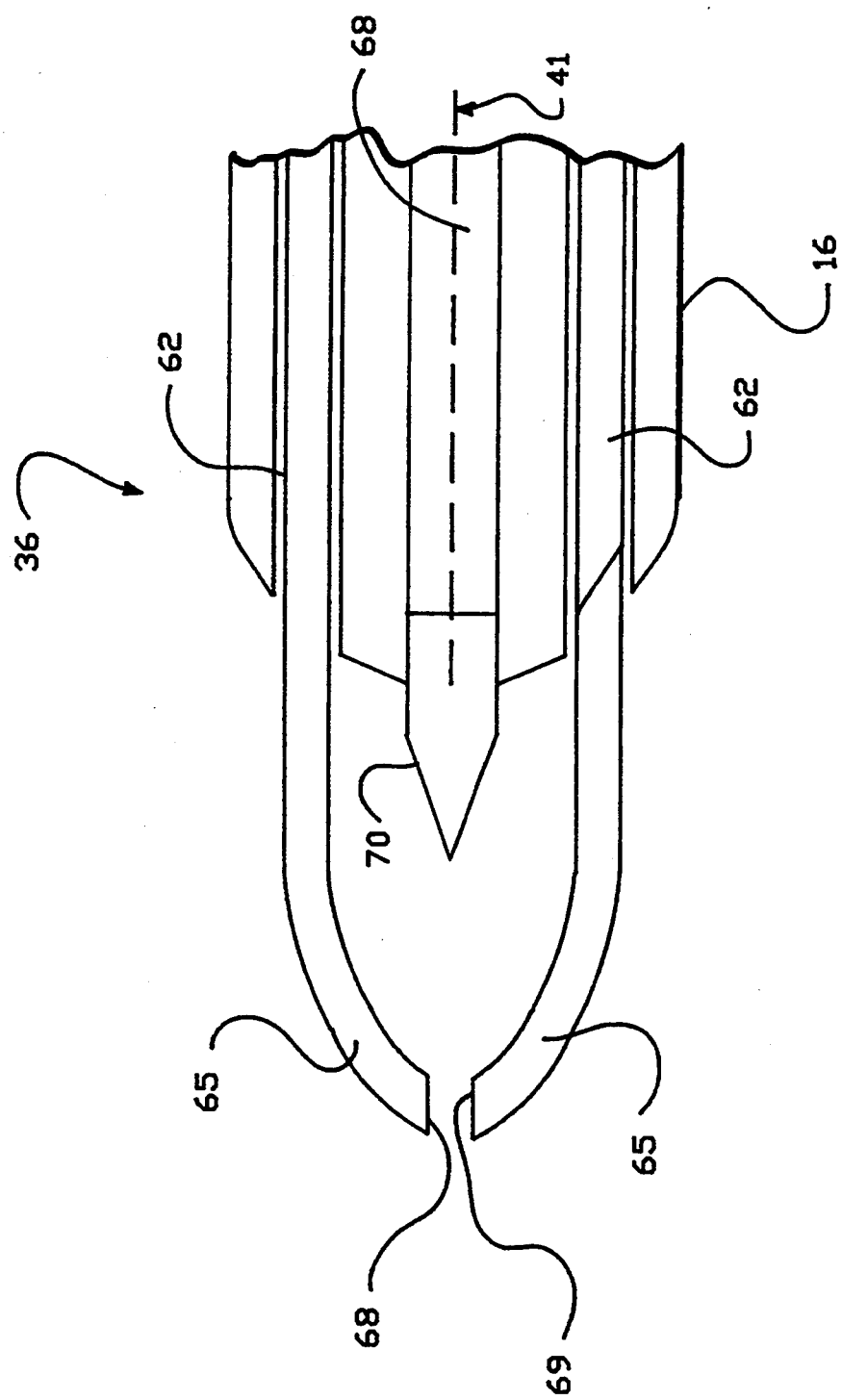
FIG. 6 illustrates the tip of the laser probe shown in FIG. 5 wherein the distal ends of the electrodes are extended.

FIG. 6 illustrates the distal end 36 of an alternative embodiment of the elongated member 16, wherein the elongated electrodes 62 are almost fully extended. FIG. 6 illustrates how the distal ends 65 of the elongated electrode 62 may be pre-bent in order to converge toward each other as the distal ends 65 are extended past the distal end 36 of the elongated member 16. This feature of convergence of the distal ends 65 enables a surgeon to both precisely cauterize specific areas of body tissue and also gently "grab" body tissue by utilizing a "tweezer" action by placing the tines of the bipolar in close contact or by applying convergent pressure to the tissue while cauterizing. It also provides a means grasping tissue for manipulation when the electrocutive function is not being utilized. Also, after closed, these members contact at facing surfaces 68, 69, and function as a monopolar electrode by appropriate switching control of the unit.

Figure 7:
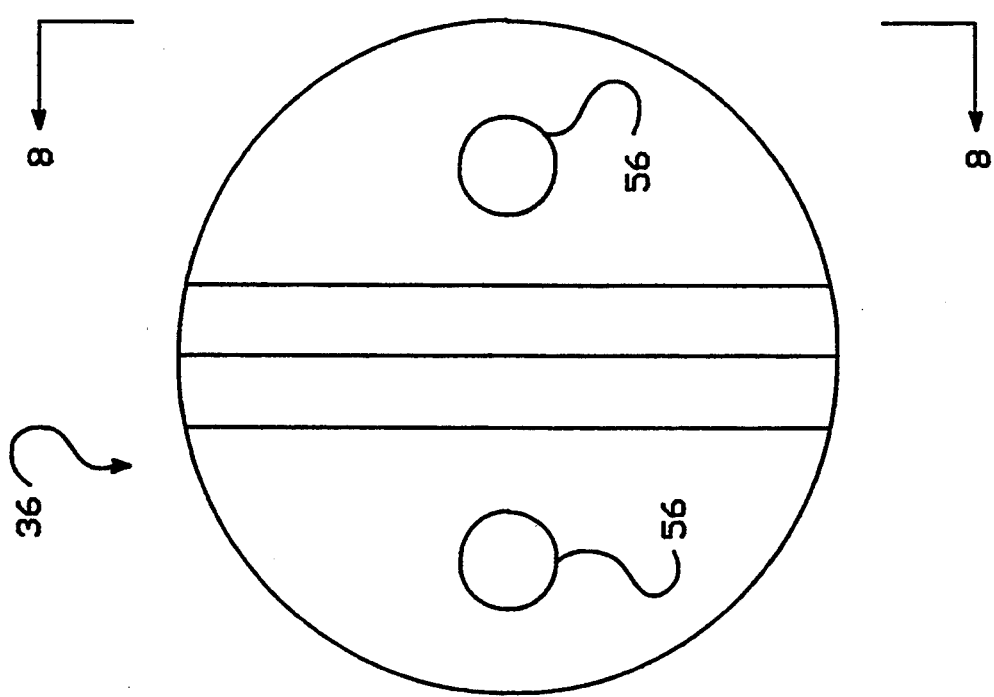
FIG. 7 is an end view of a further embodiment of the laser probe shown in FIG. 1.

FIG. 7 illustrates an end view of a further embodiment of the distal end 36 of the elongated member 16. FIG. 7 illustrates a cutting tip 80 that forms a blade in order to enable a surgeon to more easily cut and dissect or separate body tissue using the tip 80. The tip 80 is a variance of the form of the tip 70 shown in FIGS. 5 and 6. FIG. 7 also illustrates the electrode lumens 56, wherein the elongated electrodes and other lumens have been omitted from FIG. 7 for clarity.

Figure 8:
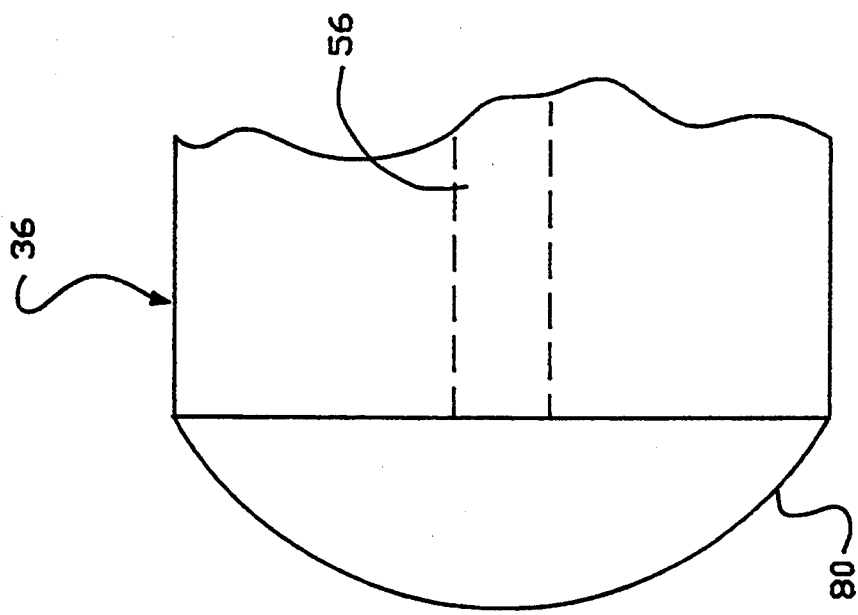
FIG. 8 is a side view of the distal end of the laser probe of FIG. 7 taken along line 8—8.

FIG. 8 illustrates a side view of the distal end 36 of the elongated member 16 shown in FIG. 7. FIG. 8 is provided in order to more clearly illustrate the blade of the tip 80. In a preferred embodiment, the tip 80 forms a semi-circle or such other configuration that provides an effective tip for dissection.

In addition to having a blade tip 80, a tip of the elongated member 16 may have varying formations depending on the intended use of the probe 10.

In practicing the endoscopic applications of the present invention, a surgeon first inserts the elongated member 16 into the body of a patient and positions the distal end 86 near the body tissue to be treated. While the electrodes 62 are in their retracted position 64, the surgeon uses the laser source 24 in conjunction with the fiber optic 68 to perform the desired procedure, such as cutting or ablating body tissue. The surgeon may also irrigate and aspirate the treated body tissue using the liquid source 18 and suction source 20 in conjunction with the lumens 58 and 60 of the elongated member 16.

In accordance with the method of the present invention, the surgeon uses the same tool 10 to cauterize the treated tissue by direct application of electric current if laser coagulation is ineffective. For example, by squeezing the trigger 14 of the handle 12 (FIG. 1 ), the distal ends 65 of the elongated electrodes 62 slide from the retracted position 64 to the extended position 66, wherein the extended position 66 places the distal ends 65 of the electrodes 62 beyond the distal end 36 of the elongated member 16. The distal ends 65 are then placed in contact with the body tissue to be cauterized and an electric potential is applied across the electrodes 62 in order to apply an electric current through a portion of the body tissue to be cauterized.

The retracting aspect of the electrodes in the present invention prevent the electrodes from obstructing non-cauterization procedures, and further enables the electrodes to be effectively positioned during cauterization procedures. This aspect enables a surgical tool configured in accordance with the present invention to effectively function as both a laser cutting and electric cauterizing tool.

Accordingly, the present invention provides an apparatus and method for cutting, irrigating, aspirating, ablating, and cauterizing via laser energy, electric current, and argon beam coagulation with a single surgical tool, thereby eliminating the necessity for inserting additional probes to perform cauterization function.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

I claim:

1. A surgical instrument comprising:
    an elongated member having a proximal end and a distal end;
    a pair of elongated electrodes having proximal ends and distal ends;
    means for slidably securing the elongated electrodes to the elongated member, wherein the elongated electrodes slide lengthwise in a direction substantially parallel to the elongated member and the distal ends of the elongated electrodes are capable of sliding beyond the distal end of the elongated member;
    first energy delivery means, coupled with the elongated member, for communicating electromagnetic energy at a first wavelength to the distal end of the elongated member; and
    second energy delivery means, coupled with the elongated member, for communicating electromagnetic energy at a second wavelength to the distal end of the elongated member.

2. A surgical instrument comprising:
    an elongated member having a proximal end and a distal end;
    a pair of elongated electrodes having proximal ends and distal ends;
    means for slidably securing the elongated electrodes to the elongated member, wherein the elongated electrodes slide lengthwise in a direction substantially parallel to the elongated member and the distal ends of the elongated electrodes are capable of sliding beyond the distal end of the elongated member;
    an optical fiber, coupled with the elongated member, for communicating electromagnetic energy to the distal end of the elongated member; and
    a transparent, sharp edged tip secured to the distal end of the elongated member and at a region near a distal end of the optical fiber, wherein electromagnetic radiation is capable of passing out the distal end of the optical fiber and passing through the tip.

3. The surgical instrument of claim 2, wherein the sharp edged tip is configured to form a blade.

4. The surgical instrument of claim 2, wherein the tip is constructed of quartz.

5. A laser probe, comprising an elongated member having a proximal end and a distal end;

an optical fiber located longitudinally within the elongated member for communicating electromagnetic energy to and out of the distal end of elongated member;

a pair of elongated electrodes having proximal ends and distal ends, the distal ends being present so as to converge on each other when extended beyond the distal end of the elongated member;

means for slidably securing the elongated electrodes to the elongated member, wherein the elongated electrodes slide lengthwise in a direction parallel to the elongated member and the distal ends of the electrodes are capable of sliding beyond the distal end of the elongated member; and a handle on the proximal end of the elongated member, the handle including an actuator and means for sliding the elongated electrodes in response to movement of the actuator.

* * * * *